United States Patent [19]

Altshuler

[11] Patent Number: 5,415,188

[45] Date of Patent: May 16, 1995

[54] DISPENSER FOR DENTAL FLOSS AND THE LIKE

[76] Inventor: Alexander Altshuler, 16 Fowler Ave., Pawtucket, R.I. 02860

[21] Appl. No.: 120,795

[22] Filed: Sep. 15, 1993

[51] Int. Cl.$^6$ .............................................. A61C 15/04
[52] U.S. Cl. ..................................... 132/325; 132/323
[58] Field of Search ................. 132/323, 324, 325, 326

[56] References Cited

U.S. PATENT DOCUMENTS

| | | | |
|---|---|---|---|
| 2,381,530 | 8/1945 | Dembenski | 132/325 |
| 4,245,658 | 1/1981 | Lecouturier | 132/322 |
| 4,518,000 | 5/1985 | Leverette | 132/325 |
| 5,038,806 | 8/1991 | Ewald | 132/324 |
| 5,060,681 | 10/1991 | Westbrook et al. | 132/324 |
| 5,085,236 | 2/1992 | Odneal et al. | 132/325 |
| 5,188,133 | 2/1993 | Romanus | 132/325 |

FOREIGN PATENT DOCUMENTS 1000533 11/1976 Canada .................... 132/325

*Primary Examiner*—Paul J. Hirsch

[57] ABSTRACT

A dispenser for dental floss and other flexible elongated materials (e.g., tape, strip, wire, etc.) capable of delivering material to the point of use under substantially constant tension. The dispenser comprises a delivery reel and a draw-in reel mechanically connected by driving means through a tension accumulator. The tension accumulator is a device comprising some means for storing energy of rotational movement (e.g. torsion spring, clock spring, etc.). Each of the reels is attached to one of the two one-way clutches so that the delivery reel can only rotate in the direction of unwinding the floss and the draw-in reel can only rotate in the direction of winding the floss on. A supply of dental floss is stored on the delivery reel and is extended under tension between the delivery reel and the draw-in reel by means of guides. Any forceful nonelastic elongation of the extended part of floss leads to unwinding a new portion of floss from the delivery reel and adding some energy to the tension accumulator; consequent release of the elongating force causes a portion of used floss of the same length to be wound on the draw-in reel by the energy freed from the tension accumulator. Such cycles of applying and releasing of the elongating force constitute continuous feeding of dental floss under tension.

13 Claims, 2 Drawing Sheets

U.S. Patent  May 16, 1995  Sheet 1 of 2  5,415,188

DISPENSER FOR DENTAL FLOSS AND THE LIKE

FIELD OF THE INVENTION

The invention relates to a dispenser for dental floss and other flexible elongated materials, and, more specifically, to a dispenser which keeps material under tension while it is continuously feeding and removing used material from the area of use.

BACKGROUND OF THE INVENTION

A number of different design solutions are currently employed for dispensing of dental floss and other flexible elongated materials. None of them is free from some drawbacks.

For instance, functioning of-most of the known in this field devices (such as U.S. Pat. Nos. 3,861,406, 5,020,554, 5,038,806, 5,060,681, 5,188,133, or "Floss-Mate" by John O. Butler Co.) which require to anchor floss under tension after it was fed comprises a chain of consequent actions performed either manually, that complicates exploitation, or by special mechanisms, that complicates the device itself.

Devices of another group (such as U.S. Pat. Nos. 4,790,336 and 5,141,008) combine feeding and tensioning functions by employing so called differential material feeding mechanisms with supply and take-up capstans of different diameters. These devices, though quite simple in design, still require frequent interruptions for tensioning/feeding and for used floss disposing.

Besides that, all of the above mentioned devices share two other deficiencies inherited from their design. First, if due to its stretchability floss gets too loose in a course of teeth cleaning manipulations, it has to be refed again in order to restore desired tension at the area of use. Second, because of relatively high floss tension required by those devices to function the length of floss in the area of use resembles a straight line segment which can only have one point contact with a generally convex surface of a tooth, thus reducing efficiency of a teeth cleaning process.

Still a device like one disclosed in U.S. Pat. No. 3,734,107 with the differential feeding mechanism, though provides some means for taking up some very limited amount of slack in stretched floss, nevertheless retains all other drawbacks of its group described above.

Yet the dental floss applicator described in U.S. Pat. No. 3,906,963, despite providing good floss tension control means for improved teeth cleaning efficiency, still fails to relieve a user of floss feeding, floss anchoring, and used floss disposing chores.

OBJECTS OF THE INVENTION

Accordingly, it is an object of this invention to provide a new and improved dispenser for dental floss and other flexible elongated materials.

Another object of the invention is to provide a dispenser for dental floss and other flexible elongated materials that is simple in design and economical in manufacturing.

Another object of the invention is to provide a dispenser capable to maintain substantially constant tension of dental floss and the like during both advancing and using of floss throughout the entire reel of floss supply.

Another object of the invention is to provide a dental floss dispenser that does not require of a user to perform any special action for floss advancing, tensioning, and disposing.

Yet another object of the invention is to provide a dental floss dispenser capable of engaging floss into linear contact with the convex tooth surface thus facilitating more efficient teeth cleaning.

SUMMARY OF THE INVENTION

The dispenser of present invention comprises a delivery reel and a draw-in reel mechanically connected by driving means through a tension accumulator. The tension accumulator employed in this invention is a device comprising some means for storing energy of rotational movement (e.g., torsion spring, clock spring, etc.). Each of the reels is attached to one of the two one-way clutches so that the delivery reel can only rotate in the direction of unwinding the floss and the draw-in reel can only rotate in the direction of winding the floss on. A supply of dental floss is stored on the delivery reel and is extended under tension between the delivery reel and the draw-in reel by means of guides. Any forceful nonelastic elongation of the extended part of floss leads to unwinding a new portion of floss from the delivery reel and adding some energy to the tension accumulator; consequent release of the elongating force causes a portion of used floss of the same length to be wound on the draw-in reel by the energy freed from the tension accumulator. Such cycles of applying and releasing of the elongating force constitute continuous feeding of dental floss under tension.

DETAILED DESCRIPTION OF THE PREFERRED EMBODIMENTS

Figure 1:
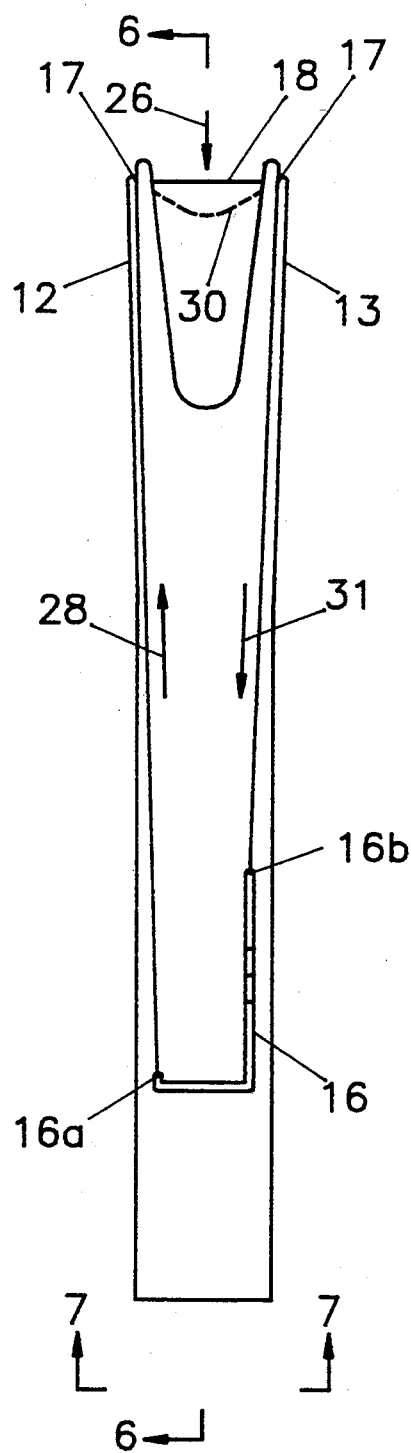
FIG. 1 is a top plan view of a dental floss disposing device in accordance with a preferred embodiment of the invention.
Figure 2:
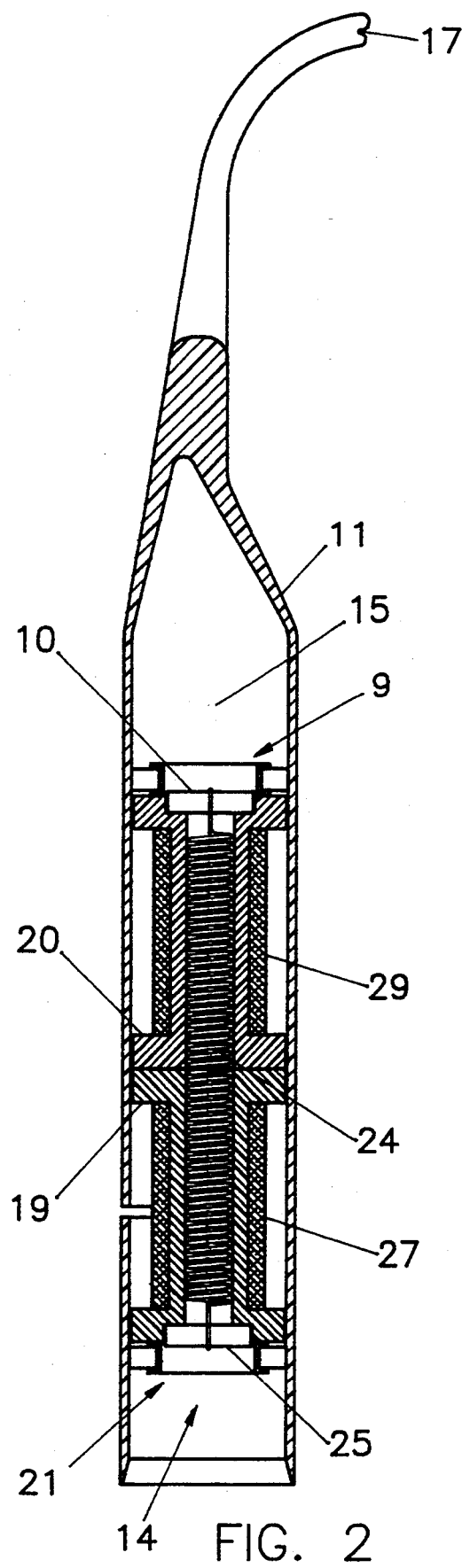
FIG. 2 is a cross-sectional view taken on line 6—6 of FIG. 1.
Figure 3:
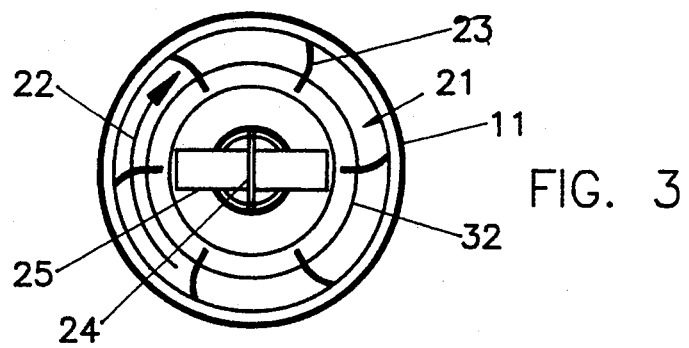
FIG. 3 is a side plan view taken on line 7—7 of FIG. 1.

A dental floss dispenser (FIGS. 1, 2, and 3) comprises a substantially cylindrical enclosure 11 with two somewhat rigid downwardly curved prongs 12 and 13 and a dental floss feeder mechanism 14 inserted into a substantially cylindrical cavity 15 of the enclosure 11 with a clearance fit. An L-shaped through wall slot 16 for initial floss threading is located on the top side of the enclosure 11. Two grooves 17 on the surface of the enclosure 11 guide an exposed length of dental floss 18 from the dispensing point 16a of the slot 16 toward the end of the prong 12 and from the end of the prong 13 toward the draw-in point 16b of the slot 16. The segment of dental floss stretched between the prongs 12 and 13 is to be utilized for teeth cleaning. The dental floss feeder mechanism 14 comprises two substantially identical hollow core delivery reel 19 and draw-in reel 20 each rigidly connected to one of two one-way clutches 21 and 9 correspondingly so that directions of unrestricted rotation (represented on the drawing by an arrow 22) coincide for both reels. A rigid plastic with a relatively low coefficient of friction is the most preferable material for the enclosure and the reels. A diversity of one-way clutch designs is known to those skilled in the art. One of the preferred embodiments of the one-way clutch comprises a polar array of flat rectangular springs 23 with one end embedded in a ring-like body 32 of the clutch and with the other end being in contact with the cylindrical inner surface of the enclosure 11. A spring 24 stretched between two pins 25 and 10 is contained in the axial hole inside the reels 19 and 20. It functions as a tension accumulator and is driven by the delivery reel 19 by means of the driving pin 25 and drives the draw-in reel 20 by means of the driving pin 10. The driving pins 25 and 10 are partially engaged in corresponding groves in flanges of the reels to prevent rotation of the pins about the axis of the reels. A close coiled helical extension spring is preferred to be used as the tension accumulator 24, although other means for torsional energy storage and for holding the reels together, such as a length of elastomeric cord, for example, can be employed without departing from the scope of the invention.

The axial length of the cavity 15 is preferably equal or exceeds 3D+2d, where D is the axial length of a reel, and d is the axial length of a one-way clutch. That will leave enough space for axial movement of the feeder mechanism 14 inside the cavity to allow each portion of a floss supply 27 be positioned in the closest proximity of the dispensing point 16a thus reducing friction in the mechanism. The distance between two ends, 16a and 16b, of the L-shaped slot 16 measured along the axis of the cavity 15 is preferably substantially equal to a distance between midpoints of the reels 19 and 20. This facilitates winding used floss on the draw-in reel in generally the same pattern as fresh floss was initially wound on the delivery reel.

The spring 24 is initially wound up to keep the exposed length of dental floss 18 under desired tension. A force (in the direction of the arrow 26, for example) can be applied to the exposed floss length 18 either in the course of cleaning in the space between teeth or intentionally to change a used segment of floss. When this force overcomes the initial tension of the spring 24 and the friction of the moving parts of the device, it draws a fresh segment of dental floss from the dental floss supply 27 on the delivery reel 19 (the floss moves in the direction of the arrow 28). The draw-in reel 20 is prevented from releasing a used dental floss 29 by the one-way clutch 9. The increased exposed length of dental floss begins to look somewhat like it is presented by a line 30. As soon as the elongating force is released, a segment of used dental floss is wound on the draw-in reel 20 by the spring 24 (the floss moves in the direction of the arrow 31). The delivery reel 19 is prevented from drawing in a segment of exposed floss by the one-way clutch 21. By multiple repetitions of the described sequence the dental floss supply 27 is gradually transferred from the delivery reel 19 through the area of use between the prongs 12 and 13 to the draw-in reel 20, where the used floss is collected, while maintaining substantially constant tension delivered by the spring 24. Accumulating and releasing of the energy of relative rotational movement of the reels are the main functions of the spring 24. Another function of the spring 24 is to hold both reels in contact with each other while still allowing their joint axial movement and individual rotational movement. Yet another function of the spring 24 is to compensate for the fluctuating difference in the angles of rotation of the two reels arising from the difference in two concurrent diameters: the diameter at which dental floss is being unwound from the delivery reel 19 and the diameter at which used dental floss is being wound on the draw-in reel 20.

Figure 4:
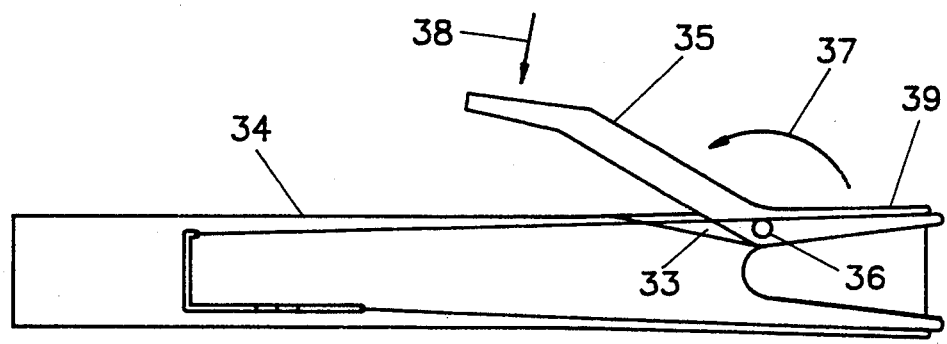
FIG. 4 is a top plan view of another preferred embodiment of the present invention.

It is not necessary for user to rely solely on teeth cleaning manipulations to create an elongating force sufficient for feeding a new length of dental floss in the area of use. In another preferred embodiment (FIG. 4) one of the prongs 39 is separate from an enclosure 34, made as one part with a handle 35, and is rotatably mounted on the enclosure 34 by means of a pivot shaft 36. A recess 33 in the enclosure is provided to allow space for rotation of the prong 39 with the handle 35 in the direction of the arrow 37 some portion of a revolution, for example 15°. Normally, the prong 39 is kept in its extreme clockwise position (shown in the FIG. 4) by the floss tension. To feed a new portion of unused floss the user presses the handle 35 in the direction of the arrow 38, rotating the prong 39 counterclockwise, thus increasing the exposed length of floss by withdrawing fresh floss from the delivery reel. When the handle 35 is released a portion of used floss is wound on the draw-in reel returning the prong 35 to its original extreme clockwise position. Because floss tension is maintained substantially constant throughout the whole floss feeding cycle, this can be done without any interruption in a teeth cleaning process. Another advantage of this embodiment of present invention is that a distance between the prongs can be conveniently adjusted for each tooth just by pressing or releasing the handle 35, thus facilitating superior cleaning.

Applications of the present invention are not limited to dental floss dispensing devices. Any flexible substantially nonstretchable elongated material (e.g., tape, rope, wire, cable, etc.) can be fed with the use of devices of this invention. The invention can be successfully used in a spectrum of different applications such as typewriter ribbon feed mechanism, a wire feeder for a hot wire cutter and a wire EDM, a strip feeder for press tool to name a few. A tape feeding mechanism in accordance with the present invention described below is yet another example of utilization of the invention.

Figure 5:
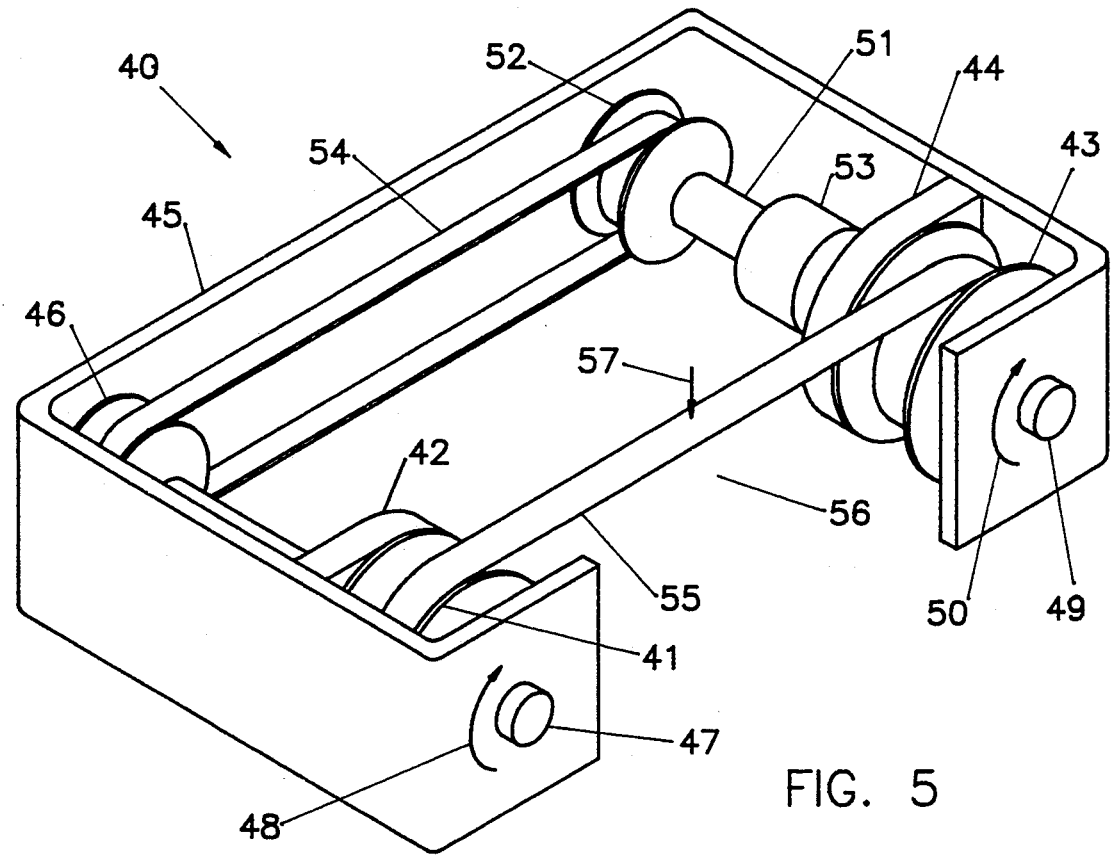
FIG. 5 is a schematic perspective view of yet another embodiment of the present invention.

A tape feeder 40 (FIG. 5) comprises a delivery reel 41 with a one-way clutch 42 and a draw-in reel 43 with a one-way clutch 44. Both one-way clutches 42 and 44 are affixed to a frame 45. The delivery reel 41 and a drive pulley 46 are mounted on a delivery shaft 47. The arrow 48 designates the direction of rotation of the delivery shaft 47 with the delivery reel 41 and the drive pulley 46 permitted by the one-way clutch 42. The draw-in reel 43 is mounted on a draw-in shaft 49. The arrow 50 designates the direction of rotation of the draw-in shaft 49 with the draw-in reel 43 permitted by the one-way clutch 44. A shaft 51 with a driven pulley 52 mounted on it is rotatably coupled to the draw-in shaft 49 by means of a power (clock) spring 53 functioning as a tension accumulator. A toothed belt 54 conveys rotational motion of the delivery shaft 47 to the shaft 51. A tape 55 is tautened between the delivery reel 41 and the draw-in reel 43 across an area of use 56 with a torque created by the initial tension of the power spring 53. A force (in the direction of the arrow 57) applied to the tape 55 during or after its use increases the length of tape between the reels 41 and 43 by unwinding a portion of tape from the delivery reel 41. Unwinding the tape from the draw-in reel 43 is restricted by the one-way clutch 44. The energy of rotational motion of the shaft 47 created by the unwinding of the tape is transferred by means of the belt drive mechanism 46, 54, and 52, to the shaft 51 additionally winding up the power spring 53 and thus accumulating there. After the force 57 is removed, a portion of the tape is wound on the draw-in reel 43 by the torque created by the power spring 53. Winding the tape on the delivery reel 41 is restricted by the one-way clutch 42. Multiple repetitions of applying and releasing the force 57 lead to a gradual advance of the tape 55 from the delivery reel 11 to the draw-in reel 43 across the area of use 56, The tape 55 stays continuously under the tension created by the power spring 53. The power spring 53 used in this embodiment of the invention delivers substantially constant torque in the desired range while compensating for the maximal possible difference in the numbers of turns performed by the delivery reel 41 and the draw-in reel 43.

Although the invention is described with respect to preferred embodiments, modifications thereto will be apparent to those skilled in the art, Therefore, the scope of the invention is to be determined by reference to the claims which follow,

What is claimed is:

1. A dispenser for flexible elongated material for use in feeding material under tension through an area of use comprising:
   rotatable delivery means for storing and releasing a supply of wound material, said delivery means having two possible reciprocal directions of rotation whereof rotation of said delivery means in one direction causes unwinding of material from said delivery means and rotation of said delivery means in the other direction causes winding of material on said delivery means;
   rotatable draw-in means for accepting, winding, and storing of material after it passed through the area of use, said draw-in means having two possible reciprocal directions of rotation whereof rotation of said draw-in means in one direction causes unwinding of material from said draw-in means and rotation of said draw-in means in the other direction causes winding of material on said draw-in means;
   a frame to support said delivery and said draw-in means in their relative position;
   first means for unidirectional restriction of rotation to prevent rotation of said delivery means relatively to said frame in the direction of winding of material on said delivery means;
   second means for unidirectional restriction of rotation to prevent rotation of said draw-in means relatively to said frame in the direction of unwinding of material from said draw-in means;
   tension accumulator means:
      for constantly applying tension to material being fed, for accumulating rotational energy of said delivery means while material is being unwound from said delivery means, and
      for releasing rotational energy to said draw-in means to wind up material from the area of use on said draw-in means;
   transmission means for transmitting rotational motion from said delivery means to said tension accumulator means and from said tension accumulator means to said draw-in means.

2. A device according to claim 1 including guiding means mounted on said frame to direct material being fed toward and from the area of use.

3. A device according to claim 1 in which said first means for unidirectional restriction of rotation and said second means for unidirectional restriction of rotation include one-way clutches.

4. A dispenser for dental floss for use in feeding dental floss under tension through an area of use comprising:
   a rotatable delivery reel for storing a supply of wound dental floss, said delivery reel having two possible reciprocal directions of rotation whereof rotation of said delivery reel in one direction causes unwinding of floss from said delivery reel and rotation of said delivery reel in the other direction causes winding of floss on said delivery reel;
   a rotatable draw-in reel for accepting, winding, and storing of used dental floss, said draw-in reel having two possible reciprocal directions of rotation whereof rotation of said draw-in reel in one direction causes unwinding of floss from said draw-in reel and rotation of said draw-in reel in the other direction causes winding of floss on said draw-in reel;
   an enclosure to contain and support in their relative position said delivery and said draw-in reels;
   first means for unidirectional restriction of rotation to prevent rotation of said delivery reel relatively to said enclosure in the direction of winding of dental floss on said delivery reel;
   second means for unidirectional restriction of rotation to prevent rotation of said draw-in reel relatively to said enclosure in the direction of unwinding of dental floss from said draw-in reel;
   tension accumulator means:
      for constantly applying tension to dental floss being fed,
      for accumulating rotational energy of said delivery reel while dental floss is being unwound from said delivery reel, and
      for releasing rotational energy to said draw-in reel to wind up dental floss from the area of use on said draw-in reel;
   transmission means for transmitting rotational motion from said delivery reel to said tension accumulator means and from said tension accumulator means to said draw-in reel;
   guiding means including a pair of prongs mounted on said enclosure to direct dental floss toward and from the area of use.

5. A device according to claim 4 in which said first means for unidirectional restriction of rotation and said second means for unidirectional restriction of rotation include one-way clutches.

6. A device according to claim 5 in which said delivery and draw-in reels have substantially cylindrical outer surfaces, and said enclosure has a substantially cylindrical cavity that accepts axially said delivery and draw-in reels with a clearance fit.

7. A device according to claim 6 in which said delivery and draw-in reels each has a hollow core and two side flanges, and said tension accumulator means have two mounting terminals; one flange of said delivery reel is rotatably adjoined to the closest flange of said draw-in reel; said tension accumulator means are disposed inside of said reels in said hollow cores and are mounted between said transmission means which anchor said mounting terminals of the tension accumulator means to the outermost flanges of said reels.

8. A device according to claim 7 in which said tension accumulator means comprise a helical extension spring.

9. A device according to claim 7 in which said tension accumulator means comprise an elastomeric cord.

10. A device according to claim 7 in which each of two said one-way clutches comprises a polar array of elongated flat springs with one end fixed to a body of said clutch and with the other end being in a sliding contact with the cylindrical inner surface of said enclosure.

11. A device according to claim 7 in which an L-shaped through wall slot in said enclosure is employed to permit transporting of dental floss in and out of said enclosure and to facilitate the initial dental floss threading procedure.

12. A device according to claim 7 in which at least one of said prongs is mounted movably on said enclosure, so that the length of dental floss stretched between reels can be changed by manipulating said prong, thus facilitating floss feeding process.

13. A device according to claim 12 in which at least one of said prongs is mounted rotatably on said enclosure, so that the distance between the ends of prongs can be changed by rotating said prong, thus facilitating more efficient teeth cleaning process.

* * * * *